United States Patent [19]
Ikeda et al.

[11] Patent Number: 6,124,454
[45] Date of Patent: Sep. 26, 2000

[54] β-FORM TRIS-(2, 3-EPOXYPROPYL)-ISOCYANURATE CRYSTALS AND PROCESS FOR THEIR PRODUCTION

[75] Inventors: Hisao Ikeda; Yasuhiro Gunji; Toshinari Koda; Motohiko Hidaka, all of Funabashi; Atsumi Aoki, Onoda, all of Japan

[73] Assignee: Nissan Chemical Industries, Ltd., Tokyo, Japan

[21] Appl. No.: 09/292,850

[22] Filed: Apr. 16, 1999

[30] Foreign Application Priority Data

Apr. 20, 1998 [JP] Japan ................................. 10-109204
Mar. 5, 1999 [JP] Japan ................................. 11-58363

[51] Int. Cl.[7] ............................................. C07D 251/30
[52] U.S. Cl. ................................................ 544/221
[58] Field of Search ............................................. 544/221

[56] References Cited

U.S. PATENT DOCUMENTS

| | | | |
|---|---|---|---|
| 3,300,490 | 1/1967 | Budnowski et al. | 544/221 |
| 3,454,570 | 7/1969 | Schwarzer | 544/221 |
| 3,547,918 | 12/1970 | Porret et al. | 544/221 |
| 5,892,065 | 4/1999 | Tsukamoto et al. | 544/221 |

FOREIGN PATENT DOCUMENTS

| | | |
|---|---|---|
| 0 232 869 | 8/1987 | European Pat. Off. . |
| 2 054 665 | 5/1971 | Germany . |

OTHER PUBLICATIONS

Derwent Abstract, AN 94–163919, JP 6–107659, Apr. 19, 1994.

Vargha et al. Angew. Makromol. Chem. 228,25–40, 1995.

CAPLUS abstract 123: 285919,1995.

*Primary Examiner*—Mukund J. Shah
*Assistant Examiner*—Venkataraman Balasubramanian
*Attorney, Agent, or Firm*—Oblon, Spivak, McClelland, Maier & Neustadt, P.C.

[57] ABSTRACT

β-form tris-(2,3-epoxypropyl)-isocyanurate crystals containing from 2 to 15 wt % of α-form tris-(2,3-epoxypropyl)-isocyanurate in the interior of the crystals.

11 Claims, No Drawings

β-FORM TRIS-(2, 3-EPOXYPROPYL)-ISOCYANURATE CRYSTALS AND PROCESS FOR THEIR PRODUCTION

The present invention relates to β-form tris-(2,3-epoxypropyl)-isocyanurate crystals and a process for their production. Particularly, it relates to a process for producing such crystals efficiently as a product of high purity wherein the content of α-form tris-(2,3-epoxypropyl)-isocyanurate which is present on the surface of the crystals in a form to be extracted by an alcohol, is not more than 2 wt %, and epichlorohydrin hazardous to human bodies or to applications to electronic materials, is reduced to a level of not more than 1,000 ppm.

In view of an increasing demand in recent years for the properties required for a solder resist material, such as adhesion, electrical insulating properties, soldering heat resistance and solvent resistance, a solder resist ink composition is presently used which is a combination of a photosensitive prepolymer and a thermosetting resin. Namely, it is designed to satisfy the above required properties by forming a solder resist pattern by the photosensitive prepolymer, followed by thermosetting. Further, demands have been increasing for high densification of printed circuit boards along with a trend for light weight and miniaturization of electronic appliances in recent years, for low bleeding during formation of solder resist patterns for surface mounting of parts and for precision in embedding between circuits. Accordingly, as the thermosetting resin to be incorporated to the solder resist ink, a fine particulate solid epoxy having high solvent resistance is desired.

As a solid epoxy to satisfy the above required properties, tris-(2,3-epoxypropyl)-isocyanurate may be mentioned. Tris-(2,3-epoxypropyl)-isocyanurate has three asymmetric carbon atoms, and crystals made of an equimolar mixture of (2R,2'R,2"R)-tris-(2,3-epoxypropyl)-isocyanurate and (2S,2'S,2"S)-tris-(2,3-epoxypropyl)-isocyanurate, wherein all of the three asymmetric carbon atoms are optically isotropic, are commonly called β-form crystals and known to give crystals having a high melting point of a level of about 150° C. This is attributable to the fact that a pair of these two types of enantiomers form a molecular lattice having firm six hydrogen bonds and thus form a crystal lattice. On the other hand, crystals made of a mixture of (2R,2R,2S)-tris-(2,3-epoxypropyl)-isocyanurate and (2S,2S,2R)-tris-(2,3-epoxypropyl)-isocyanurate, wherein one of the three asymmetric carbon atoms is different in the optical anisotropy, are commonly called α-form crystals, and they do not have the above crystal structure and accordingly present only a low melting point of a level of about 100° C. The β-form tris-(2,3-epoxypropyl)-isocyanurate crystals not only have a high melting point but also have a low solubility in various solvents. Accordingly, when they are used as a crosslinking agent for different types of compounds or for reactive polymers in the form of a one pack type reactive mixture, the reaction will not proceed during the storage, until they are forcibly cured. Such β-form crystals have been used for applications to electric and electronic materials, for example, as a solder resist ink composition of photocuring/thermosetting combined type.

The liquid epoxy composition is likely to undergo an increase in the viscosity during storage, since a part of the epoxy compound dissolves in the solvent, and entanglement with the photosensitive prepolymer is likely to result, whereby elution tends to be poor during washing off of the non-exposed portion. JP-B-7-17737 discloses use of β-form tris-(2,3-epoxypropyl)-isocyanurate as a hardly soluble epoxy compound. β-form tris-(2,3-epoxypropyl)-isocyanurate fine particles which have a high melting point and which are hardly soluble, are in a state enclosed by a photosensitive prepolymer, whereby they will not reduce the solubility of the photosensitive prepolymer at the non-exposed portion. Further, they are hardly soluble in an organic solvent, whereby the exposed portion is hardly eroded by a developer, whereby there will be no deterioration in the sensitivity. Further, the storage stability of the solder resist ink composition is excellent.

As a method for separating β-form tris-(2,3-epoxypropyl)-isocyanurate and α-form tris-(2,3-epoxypropyl)-isocyanurate from tris-(2,3-epoxypropyl)-isocyanurate, a separation method has been available wherein a solvent which dissolves α-form tris-(2,3-epoxypropyl)-isocyanurate relatively well and which hardly dissolves β-form tris-(2,3-epoxypropyl)-isocyanurate, for example, an alcohol such as methanol, is employed. For example, Journal of Thermal Analysis, vol. 36 (1990) p. 1819 discloses separation by means of a methanol solvent Further, Plaste und Kautschuk 23 Jahrgang Heft 4/1975 discloses a method wherein firstly a methanol solvent is used for separating β-form tris-(2,3-epoxypropyl)-isocyanurate, and then the β-form tris-(2,3-epoxypropyl)-isocyanurate is purified by chloroform Further, Kobunshi Ronbunshu (polymer report collection), vol. 47, No. 3 (1990) p. 169, discloses a method wherein synthesized tris-(2,3-epoxypropyl)-isocyanurate is put into methanol, followed by heating and stirring, whereupon the non-dissolved content is collected by filtration, and the obtained non-dissolved substance is re-crystallized from methyl ethyl ketone to obtain β-form tris-(2,3-epoxypropyl)-isocyanurate crystals.

Many of β-form tris-(2,3-epoxypropyl)-isocyanurates obtained by such separation methods, hardly undergo crystal growth, and many of them have an average particle size of less than 10 μm. In the filtration step, if the diameters of openings of the filter material are 10 μm or larger, the yield will be very poor, as there will be a substantial amount of particles which pass through the filter material. On the other hand, if the diameters of openings of the filter material are smaller than 10 μm, the filtration resistance tends to be large, and clogging of the filter material is likely to occur, whereby the filtration operation tends to be very difficult.

Further, by a single separation operation by the foregoing separation method, β-form tris-(2,3-epoxypropyl)-isocyanurate tends to contain chlorine-containing impurities or other impurities as well as α-form tris-(2,3-epoxypropyl)-isocyanurate. Accordingly, it will be necessary to further carry out recrystallization.

JP-B-48-24039 discloses a process wherein a chlorohydrin ester of isocyanuric acid obtained by reacting cyanuric acid with epichlorohydrin, is dehydrochlorinated with an alkali, and the alkali metal chloride thereby formed, is separated, and the obtained epichlorohydrin solution of tris-(2,3-epoxypropyl)-isocyanurate, is concentrated to a tris-(2,3-epoxypropyl)-isocyanurate concentration of from 50 to 60%, and then the solution was cooled to from 20 to 25° C. to obtain tris-(2,3-epoxypropyl)-isocyanurate crystals in an yield of 27% based on cyanuric acid. The tris-(2,3-epoxypropyl)-isocyanurate obtainable by a conventional process is known to contain α-form tris-(2,3-epoxypropyl)-isocyanurate and β-form tris-(2,3-epoxypropyl)-isocyanurate in a ratio of 3:1.

The yield of β-form tris-(2,3-epoxypropyl)-isocyanurate present at the reaction stage of JP-B-48-24039 is expected to be at most 20% based on cyanuric acid, and at the stage after the crystallization, the yield is expected to be at most 19% based on cyanuric acid. Whereas, the tris-(2,3-epoxypropyl)-isocyanurate crystals obtained in JP-B-48-24039 is 27% in yield based on cyanuric acid, from which the proportion of α-form tris-(2,3-epoxypropyl)-isocyanurate in the obtained crystals is calculated to be at least (27%–19%)/27%×100 =30%. The results of a duplication test carried out by the present inventors also showed that the content of α-form tris-(2,3-epoxypropyl)-isocyanurate was at least 30%. It is considered that in the crystals obtained in JP-B-48-24039, a substantial amount of α-form tris-(2,3-epoxypropyl)-isocyanurate is attached on the surface of β-form tris-(2,3-epoxypropyl)-isocyanurate crystals or is present in the form of independent crystals.

Thus, the above process has a problem that the crystals contain a large amount of α-form tris-(2,3-epoxypropyl)-isocyanurate in the form to be extracted by an alcohol, and further a few thousands ppm of epichlorohydrin, etc. are contained in the interior of the crystals. Namely, as mentioned above, alcohol-soluble α-form tris-(2,3-epoxypropyl)-isocyanurate is present on the surface of the β-form tris-(2,3-epoxypropyl)-isocyanurate crystals or is independently present, whereby there is a problem that it dissolves in a solder resin composition to deteriorate the storage stability or to deteriorate the developability. Further, epichlorohydrin is composed of a hydrolyzable chlorine which is not only hazardous to human bodies but also hazardous to applications to electronic materials, and should be contained as little as possible.

The object of the present invention is to obtain β-form tris-(2,3-epoxypropyl)-isocyanurate by industrially advantageous crystallization of a reaction solution of tris-(2,3-epoxypropyl)-isocyanurate, and more particularly, to obtain β-form tris-(2,3-epoxypropyl)-isocyanurate wherein α-form tris-(2,3-epoxypropyl)-isocyanurate in the form to be extracted by an alcohol is at most 2 wt % of the total tris-(2,3-epoxypropyl)-isocyanurate, and the remaining epichlorohydrin is reduced to a level of not more than 1,000 ppm, particularly not more than 300 ppm.

In the first aspect, the present invention provides β-form tris-(2,3-epoxypropyl)-isocyanurate crystals containing from 2 to 15 wt % of α-form tris-(2,3-epoxypropyl)-isocyanurate in the interior of the crystals.

In the second aspect, the present invention provides the β-form tris-(2,3-epoxypropyl)-isocyanurate crystals according to the first aspect, which have an average particle size of from 10 to 500 μm.

In the third aspect, the present invention provides a process for producing β-form tris-(2,3-epoxypropyl)-isocyanurate crystals containing from 2 to 15 wt % of α-form tris-(2,3-epoxypropyl)-isocyanurate in the interior of the crystals, which comprises the following steps (A), (B), (C), (D) and (E)

(A) a step of reacting 1 mol of cyanuric acid with from 5 to 180 mols of epichlorohydrin to form an addition product of cyanuric acid and epichlorohydrin, followed by dehydrochlorination to obtain a reaction solution containing tris-(2,3-epoxypropyl)-isocyanurate, (B) a step of adjusting the reaction solution containing tris-(2,3-epoxypropyl)-isocyanurate obtained in step (A) to a solid content concentration of from 10 to 50 wt %, (C) a step of adding seed crystals to the liquid obtained in step (B) at a temperature lower by from 5 to 20° C. than the temperature at which the liquid forms a saturated solution, (D) a step of gradually cooling the liquid obtained in step (C) at a cooling rate of not higher than 20° C./hr for crystallization, followed by filtration to obtain crystals, and (E) a step of washing and drying the crystals obtained in step (D).

In the fourth aspect, the present invention provides the process according to the third aspect, wherein step (A) is a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a trisubstituted phosphine and a quaternary phosphonium salt, as catalyst, to obtain a reaction solution, adding from 2 to 6 mols of an alkali metal hydroxide or an alkali metal alcoholate to the reaction solution for dehydrochlorination, and then removing the resulting alkali metal salt to obtain a reaction solution containing tris-(2,3-epoxypropyl)-isocyanurate.

In the fifth aspect, the present invention provides the process according to the third or fourth aspect, wherein step (C) is a step of heating the liquid obtained in step (B) to a temperature of at least the temperature at which the liquid forms a saturated solution, thereafter cooling the liquid to a temperature lower by from 5 to 20° C. than the temperature at which the liquid forms a saturated solution, and then adding seed crystals thereto.

In the sixth aspect, the present invention provides the process according to any one of the third to fifth aspects, wherein the addition of seed crystals in step (C) satisfies the following formulae (1) and (2):

$$1 \times 10^{10} \geq T \geq 1 \times 10^2 \qquad (1)$$

$$T = 1.4 \times 10^{12} \, (m/(M \times D^3)) \qquad (2)$$

wherein T is the number of seed crystals added per the weight of tris-(2,3-epoxypropyl)-isocyanurate in the reaction solution (number/g), m is the amount of seed crystals added (g), D is the average particle size of seed crystals which is from 2 to 300 μm, and M is the weight (g) of tris-(2,3-epoxypropyl)-isocyanurate in the reaction solution.

In the seventh aspect, the present invention provides the process according to any one of the third to sixth aspects, wherein the seed crystals added in step (C) is β-form tris-(2,3-epoxypropyl)-isocyanurate, or a mixture of β-form tris-(2,3-epoxypropyl)-isocyanurate and α-form tris-(2,3-epoxypropyl)-isocyanurate.

In the eighth aspect, the present invention provides the process according to any one of the third to seventh aspects, wherein ultrasonic waves are applied to the liquid in the process of gradually cooling the liquid in step (D).

In the ninth aspect, the present invention provides the process according to any one of the third to eighth aspects, wherein a solvent capable of providing a solubility of at least 0.5 g/100 g at 20° C. to α-form tris-(2,3-epoxypropyl)-isocyanurate and a solubility of less than 0.5 g/100 g at 20° C. to β-form tris-(2,3-epoxypropyl)-isocyanurate, is used in an amount of from 0.5 to 10 times by weight relative to the β-form tris-(2,3-epoxypropyl)-isocyanurate crystals.

In the tenth aspect, the present invention provides the process according to any one of the third to ninth aspects, wherein the average particle size of the crystals obtained in step (D) is from 20 to 500 μm, and the drying in step (E) is carried out under atmospheric pressure or under reduced pressure in a gas stream at a temperature of from 120 to 140° C.

In the eleventh aspect, the present invention provides the process according to any one of the third to ninth aspects, wherein the average particle size of the crystals obtained in step (D) is from 10 to 20 μm, and the drying in step (E) is carried out under atmospheric pressure or under reduced pressure in a gas stream at a temperature of from 40 to 120° C.

Now, the present invention will be described in detail with reference to the preferred embodiments.

In the present invention, the β-form tris-(2,3-epoxypropyl)-isocyanurate crystals containing from 2 to 15 wt % of α-form tris-(2,3-epoxypropyl)-isocyanurate in the interior of the crystals, are obtainable as having an average particle size of from 10 to 500 μm. The content of α-form tris-(2,3-epoxypropyl)-isocyanurate present in the interior of the α-form tris-(2,3-epoxypropyl)-isocyanurate crystals is from 2 to 15 wt %, preferably from 4 to 13 wt %, as a proportion of (α-form)/(α-form+β-form).

As a method for measuring the content of α-form tris-(2,3-epoxypropyl)-isocyanurate present independently or on the surface of the β-form tris-(2,3-epoxypropyl)-isocyanurate crystals of the present invention, a solvent extraction method is, for example, available. Since the β-form has a very small solubility in an organic solvent as compared with the α-form, the measurement can be carried out with high precision. As the organic solvent to be used here, an alcohol type solvent such as methanol or ethanol may, for example, be mentioned.

Further, as a method for measuring the ratio of the α-form and the β-form in the entire crystals, $^1$H-NMR, IR or a method by HPLC by means of an optical resolution column, is available. As the optical resolution column, an amylose or cellulose derivative may be used as the stationary phase, whereby resolution can efficiently be carried out, and the measurement can be carried out with high precision.

The α-form tris-(2,3-epoxypropyl)-isocyanurate contained in the β-form tris-(2,3-epoxypropyl)-socyanurate crystals of the present invention is from 2 to 15 wt %, and the analytical method is not limited to the method disclosed in this application.

The α-form tris-(2,3-epoxypropyl)-isocyanurate contained in the interior of the β-form tris-(2,3-epoxypropyl)-isocyanurate crystals will not be extracted by an organic solvent such as methanol, and when formed into an epoxy resin composition, it will not elute from the β-form tris-(2,3-epoxypropyl)-isocyanurate crystals.

In the process for producing β-form tris-(2,3-epoxypropyl)-isocyanurate crystals of the present invention, step (A) is a step of reacting 1 mol of cyanuric acid with from 5 to 180 mols of epichlorohydrin to form an addition product of cyanuric acid and epichlorohydrin, followed by dehydrochlorination to obtain a reaction solution containing tris-(2,3-epoxypropyl)-isocyanurate. More specifically, step (A) is a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a trisubstituted phosphine and a quaternary phosphonium salt, as a catalyst, to obtain a reaction solution, adding from 2 to 6 mols of an alkali metal hydroxide or an alkali metal alcoholate to the reaction solution for dehydrochlorination, and then removing the resulting alkali metal salt to obtain a reaction solution containing tris-(2,3-epoxypropyl)-isocyanurate.

In step (A), the catalyst for addition of epichlorohydrin to cyanuric acid is not particularly limited, and it may, for example, be a tertiary amine, a quaternary ammonium salt, a quaternary ammonium base, a trisubstituted phosphine or a quaternary phosphonium salt. It is preferred to use from 0.001 to 0.1 mol of the catalyst per mol of cyanuric acid. As examples of the catalyst, the tertiary amine may, for example, be tripropylamine, tributylamine or N,N'-dimethylpiperazine. The quaternary ammonium salt may, for example, be tetramethylammonium halide, tetraethylammonium halide or tetrabutylammonium halide, wherein the halide may, for example, be chloride, bromide or iodide. The quaternary ammonium base may, for example, be tetramethylammonium hydroxide, or benzyltrimethylammonium hydroxide. The tri-substituted phosphine may, for example, be tripropylphosphine, tributylphosphine, triphenylphosphine or tritolylphosphine, and the quaternary phosphonium salt may, for example, be tetramethylphosphonium halide, tetrabutylphosphonium halide, methyltriphenylphosphonium halide or ethyltriphenylphosphonium halide, wherein the halide may, for example, be chloride, bromide or iodide. Among the above mentioned compounds, a quaternary ammonium salt or a quaternary phosphonium salt is particularly preferred since the reaction proceeds efficiently under a mild condition with no substantial side reaction. Particularly preferred is a quaternary ammonium, such as tetramethylammonium halide, tetraethylammonium halide or tetrabutylammonium halide, wherein the halide is chloride or bromide, whereby the side reactions can be suppressed, and removal of the catalyst after the reaction can easily be made simply by washing with water.

Further, in step (A), by the subsequent dehydrochlorination, a reaction solution containing tris-(2,3-epoxypropyl)-isocyanurate can be obtained. The reagent to be used for this dehydrochlorination reaction is not particularly limited, and it may, for example, be an alkali metal hydroxide or an alkali metal alcoholate. It is preferred to use an alkali metal hydroxide or an alkali metal alcoholate in an amount within a range of from 2 to 6 mols, preferably from 2.5 to 4 mols, per mol of cyanuric acid. As such an alkali metal hydroxide, sodium hydroxide, potassium hydroxide or lithium hydroxide may, for example, be mentioned, and as such an alkali metal alcoholate, sodium methylate, sodium ethylate, potassium methylate or potassium ethylate may, for example, be mentioned. The tris-(2,3-epoxypropyl)-isocyanurate thus obtained, contains β-form tris-(2,3-epoxypropyl)-isocyanurate and 60-form tris-(2,3-epoxypropyl)-isocyanurate in a weight ratio of 1:3.

The reaction solution containing tris-(2,3-epoxypropyl)-isocyanurate thus obtained, is then adjusted by concentration or dilution to a concentration suitable for crystallization. For the measurement of the solid content concentration, the reaction solution is treated by a rotary evaporator at 120° C. under a pressure of not higher than 5 Torr for 3 hours for evaporation to dryness, whereupon the solid content weight is measured, and the solid content concentration can be calculated.

In step (B), the solid content concentration of the reaction solution containing tris-(2,3-epoxypropyl)-isocyanurate is adjusted to a level of from 10 wt % to 50 wt %, preferably from 25 wt % to 40 wt %.

If this concentration is too low, the cooling temperature required for crystallization must be lowered to a low level, and no adequate yield can be attained.

On the other hand, if this concentration is too high, the cooling temperature required for crystallization must be maintained at a high temperature. Consequently, the filtration temperature must be maintained at a high temperature. Here, if the solution is cooled to a temperature lower than the final cooling temperature range, rapid crystallization will take place, and it is likely to take in 60-form tris-(2,3-epoxypropyl)-isocyanurate, such being undesirable. Further, if the concentration is too high, the change in the solubility to the change in the temperature will be large, whereby rapid crystallization will take place, whereby it is likely to take in α-form tris-(2,3-epoxypropyl)-isocyanurate, such being undesirable.

The necessity for maintaining the cooling temperature range required for this crystallization is to let a proper amount of the α-form be selectively contained in the precipitated β-form crystals.

Table 1 shows the relation between the solid content (%) of tris-(2,3-epoxypropyl)-isocyanurate in the reaction solution, and the temperature (° C.) for forming a saturated solution and the cooling temperature (° C.) required for crystallization. Here, the temperature for forming a saturated solution is determined in such a manner that the reaction solution obtained in step (B) is evaporated to dryness at 120° C. under 2 Torr to obtain tris-(2,3-epoxypropyl)-isocyanurate, which is pulverized to obtain a powder of at most 32 mesh, which is adjusted to a predetermined solid content concentration with epichlorohydrin, followed by heating at a temperature-raising rate of 1° C./min from room temperature with vigorous stirring, whereby the temperature when the solid has dissolved completely, is taken as the temperature for forming a saturated solution.

TABLE 1

| Solid content concentration (%) of tris-(2,3-epoxypropyl)-isocyanurate | 50 | 40 | 30 | 25 | 15 | 10 |
|---|---|---|---|---|---|---|
| Temperature (° C.) for forming a saturated solution | 79 | 69 | 58 | 53 | 39 | 29 |
| Cooling temperature (° C.) required for crystallization | 35 ± 5 | 25 ± 5 | 15 ± 5 | 11 ± 5 | 0 ± 5 | −5 ± 5 |

In step (C), seed crystals are added to the liquid obtained in step (B) at a temperature lower by from 5 to 20° C. than the temperature at which this liquid forms a saturated solution. If crystallization is carried out without adding seed crystals, a supersaturated state will continue even during cooling, and at a later half of cooling, crystallization takes place all at once. This is not desirable since the purity deteriorates due to inclusion of impurities such as epichlorohydrin and α-form tris-(2,3-epoxypropyl)-isocyanurate.

In step (C), prior to the addition of seed crystals, the reaction solution may be heated to a temperature of at least the temperature for forming a saturated solution to adequately dissolve tris-(2,3-epoxypropyl)-isocyanurate in the reaction solution, and then it is gradually cooled to a temperature lower by from 5 to 20° C. than the temperature for forming a saturated solution, and then seed crystals may be added. By this method, the particle size of the obtained crystals will be uniform, such being desirable in view of the filtration properties, etc.

The addition of seed crystals in step (C) satisfies the following formulae (1) and (2):

$$1\times10^{10} \geq T \geq 1\times10^2 \quad (1)$$

$$T=10^{12}m/(M(4/3)\pi(D/2)^3 d)=1.4\times10^{12}(m/(M\times D^3)) \quad (2)$$

wherein T is the number of seed crystals per weight of tris-(2,3-epoxypropyl)-isocyanurate in the reaction solution (number/g), m is the weight (g) of seed crystals added, D is the average particle size of seed crystals which is from 2 to 300 μm, M is the weight (g) of tris-(2,3-epoxypropyl)-isocyanurate in the reaction solution, and d is the true specific gravity of tris-(2,3-epoxypropyl)-isocyanurate.

In the present invention, crystal growth starts from the added seed crystals as nuclei. The crystal size of the resulting β-form tris-(2,3-epoxypropyl)-isocyanurate can be controlled by the number of seed crystals added per weight of tris-(2,3-epoxypropyl)-isocyanurate in the reaction solution (T: number/g) as defined by the above formulae (1) and (2). The number (T) of seed crystals determined by the amount of seed crystals and the average particle size, is preferably at least $10^2$ particles/g, per weight of tris-(2,3-epoxypropyl)-isocyanurate in the reaction solution, when seed crystals having an average particle size of from 2 to 300 μm are used. If the number of seed crystals is small, the average crystal size of the crystallized β-form tris-(2,3-epoxypropyl)-isocyanurate becomes large, and if the number (T) of seed crystals is large, β-form tris-(2,3-epoxypropyl)-isocyanurate crystals having a small average particle size will be crystallized. Further, if the number (T) of seed crystals is too much beyond $1\times10^{10}$ particles per g, the average particle size of the crystallized β-form tris-(2,3-epoxypropyl)-isocyanurate will be less than 10 μm, such being undesirable. Especially when seed crystals having an average particle size exceeding 100 μm are employed, if the number (T) of seed crystals is large, the added weight tends to be too much, such being undesirable.

If step (C) is carried out without heating the reaction solution to a temperature of at least the temperature for forming a saturated solution, while maintaining it at a temperature lower by from 5 to 20° C. than the temperature for forming a saturated solution, fine crystals will be formed in the reaction solution at this temperature, and such crystals will also serve as seed crystals together with the subsequently added seed crystals, whereby it tends to be difficult to control the number (T) of seed crystals. Accordingly, it is preferred that the reaction solution is heated once to a temperature of at least the temperature for forming a saturated solution, then cooling it to a temperature lower by from 5 to 20° C. than the temperature for forming a saturated solution, and then seed crystals are added.

As the seed crystals to be added in step (C), β-form tris-(2,3-epoxypropyl)-isocyanurate, or a mixture of β-form tris-(2,3-epoxypropyl)-isocyanurate and α-form tris-(2,3-epoxypropyl)-isocyanurate, may be employed.

After adding the seed crystals in step (C), it is preferred to carry out stirring at the temperature for the addition for from 0.5 to 1 hour.

In the subsequent step (D), the liquid is gradually cooled to a temperature at which α-form tris-(2,3-epoxypropyl)-isocyanurate maintains a supersaturated state. This cooling rate is at most 2° C./hr, preferably at most 10° C./hr. It the cooling is carried out rapidly, rapid crystal precipitation will take place, and the purity will decrease due to inclusion of impurities, such being undesirable.

The precipitated β-form tris-(2,3-epoxypropyl)-isocyanurate crystals will be separated by filtration such as suction filtration, filter press filtration or centrifugal filtration.

In step (E), the β-form tris-(2,3-epoxypropyl)-isocyanurate obtained by filtration, can be washed with various organic solvents, since it contains impurities, or α-form tris-(2,3-epoxypropyl)-isocyanurate and epichlorohydrin. The organic solvents include, for example, methanol, ethanol, isopropylalcohol, methyl ethyl ketone, acetonitrile, dimethylformamide, and epichlorohydrin. Among them, an organic solvent having a low boiling point, in which the solubility of β-form tris-(2,3-epoxypropyl)-isocyanurate is less than 0.5 g/100 g at 20° C., and the solubility of α-form tris-(2,3-epoxypropyl)-isocyanurate is at least 0.5 g/100 g at 20° C., is preferred. As an organic solvent having such characteristics, methanol, ethanol or isopropyl alcohol may, for example, be mentioned.

The washing can be carried out at a temperature of from 5 to 50° C., preferably from 5 to 30° C. At a high temperature such as from 30 to 50° C., the solubility increases, and the amount of the solvent can be saved, but the operation will be at a temperature close to the boiling point or the flash point. A centrifugal filtration machine has a possible danger of inflammation due to static electricity, and a highly safe pressure filtration machine has a possible problem such that α-form tris-(2,3-epoxypropyl)-isocyanurate dissolved in the washing solvent is likely to recrystallize in the filter material or in the cake by the passage of pressurizing gas, whereby the filtration property tends to deteriorate. Further, there will be a restriction such that a preheating installation for the solvent and a temperature-keeping installation not to let α-form tris-(2,3-epoxypropyl)-isocyanurate reprecipitate from the recovered solvent, will be required. Further, at a temperature of 50° C. or higher, a special thermal filtration system will be required. On the other hand, at a temperature lower than 5° C., a large amount of the solvent will be required.

The amount for washing varies depending upon the temperature and the solvent, but it is usually from 0.5 to 10 times by weight, preferably from 1 to 6 times by weight, relative to the dry weight of the β-form tris-(2,3-epoxypropyl)-isocyanurate crystals. As the washing method, the β-form tris-(2,3-epoxypropyl)-isocyanurate obtained by filtration, may again be slurried, followed by filtration. Otherwise, the solvent may be supplied during filtration to carry out the washing.

In step (E), after the washing, drying can be carried out under atmospheric pressure or under reduced pressure in a gas stream at a temperature of from 120 to 140° C. The above reduced pressure may be various pressures so long as it is a pressure lower than atmospheric pressure, such as a pressure of from 5 to 20 Torr. Further, the drying time is usually from 2 to 24 hours.

The above temperature of from 120 to 140° C. is a temperature higher than the melting point of α-form tris-(2,3-epoxypropyl)-isocyanurate and a temperature lower than the melting point of β-form tris-(2,3-epoxypropyl)-isocyanurate. When the drying is carried out at this temperature in a gas stream, in the β-form tris-(2,3-epoxypropyl)-isocyanurate crystals containing α-form tris-(2,3-epoxypropyl)-isocyanurate in the interior of the crystals, a part of the α-form tris-(2,3-epoxypropyl)-isocyanurate will be melted and liquefied. Through this liquid portion, epichlorohydrin as an impurity will be discharged from the crystals out of the crystals. With the β-form tris-(2,3-epoxypropyl)-isocyanurate crystals containing from 5 to 15 wt % of α-form tris-(2,3-epoxypropyl)-isocyanurate in the interior of the crystals, obtained through the drying step in step (E), the remaining epichlorohydrin can be reduced to a level of at most 1,000 ppm, particularly preferably at most 3,000 ppm. The reduction of the amount of epichlorohydrin remaining in the product can be accomplished in such a manner that the α-form tris-(2,3-epoxypropyl)-isocyanurate contained in the interior of the crystals is melted at the drying temperature of from 120 to 140° C., preferably from 125 to 135° C., to form liquid pores in the interior of the crystals, and epichlorohydrin is discharged through these liquid pores out of the crystals. In order to reduce the remaining epichlorohydrin, a proper amount of α-form tris-(2,3-epoxypropyl)-isocyanurate present in the interior of the crystals and a proper washing/drying method are considered to be required. Especially with crystals having an average particle size of from 20 to 500 μm, the amount of the remaining epichlorohydrin can be substantially reduced as between before and after the drying at from 120 to 140° C. Accordingly, with crystals having an average particle size of from 20 to 500 μm, drying under atmospheric pressure or under reduced pressure in a gas stream at a temperature of from 120 to 140° C. is necessary.

If the content of the α-form tris-(2,3-epoxypropyl)-isocyanurate present in the interior of the crystals is less than 2 wt %, pores formed by melting of the α-form tris-(2,3-epoxypropyl)-isocyanurate in the interior of the crystals tend to be little, whereby the amount of epichlorohydrin remaining in the formed crystals tends to increase.

On the other hand, if the content of the α-form tris-(2,3-epoxypropyl)-isocyanurate present in the interior of the crystals exceeds 15 wt %, during the drying at from 120 to 140° C., α-form tris-(2,3-epoxypropyl)-isocyanurate tends to bleed out from the interior of the crystals and act as a binder of particles, thus leading to coagulation, such being undesirable. If coagulation of particles takes place, the drying efficiency tends to be poor, and discharge from the drier tends to be difficult, and pulverization will be required anew, such being undesirable.

When the content of the α-form tris-(2,3-epoxypropyl)-isocyanurate in the interior of the crystals is from 2 to 15 wt %, and the drying temperature is from 120 to 140° C., coagulation of crystals due to bleeding out of α-form tris-(2,3-epoxypropyl)-isocyanurate to the surface of the crystal particles will scarcely take place.

Further, α-form tris-(2,3-epoxypropyl)-isocyanurate which is present independently or on the surface of the crystals and which is in the form to be extracted by an alcohol, is preferably at most 2 wt %. If this value exceeds 2 wt %, the shape of crystals or the particle size distribution tends to be non-uniform, whereby the filtration property tends to deteriorate, or a coagulation of particles due to fusion during the drying tends to occur. Further, when made into a photo-setting/thermosetting combined one pack type resist ink composition, it tends to melt in a solvent thus leading to viscosity increase during the storage, and entanglement with the photosensitive prepolymer is likely to occur, whereby when the non-exposed portion after exposure is washed off, the elution tends to be poor.

When the α-form tris-(2,3-epoxypropyl)-isocyanurate which is present independently or on the surface of the crystals and which is in the form to be extracted by an alcohol, exceeds 2 wt % to some extent, it may be possible to reduce the value to a level of not more than 2 wt % by additional washing with e.g. methanol. However, if this value is from 10 to 20 wt %, the amount of methanol for additional washing at 20° C. will be required to be from 20 to 40 times by weight, such being an extremely inefficient method when the working efficiency and recovery or disposal of methanol are taken into consideration. If washing is carried out with heated methanol, the amount of methanol can be saved, but a centrifugal separating machine can not be used, and a pressure filtration machine has to be used, whereby the α-form tris-(2,3-epoxypropyl)-isocyanurate dissolved in methanol is likely to reprecipitate in the filter material or in the cake by the passage of the pressurizing gas, and the filtration property tends to deteriorate, and there will be a restriction from the viewpoint of installation.

In the present invention, when vigorous stirring such as ultrasonic wave vibration is applied during the crystallization in step (D), crystals having an average particle size of from 10 μm to 50 μm, particularly from 10 μm to 20 μm, will be precipitated. When the average particle size of crystals obtained in step (D) is from 10 to 20 μm, re-dissolution of α-form tris-(2,3-epoxypropyl)-isocyanurate in step (D) is likely to take place, and due to the large specific surface area of such crystals, the α-form tris-(2,3-epoxypropyl)-isocyanurate is readily removable by washing with an organic solvent in step (E). Accordingly, in the crystals obtained in step (E), the α-form tris-(2,3-epoxypropyl)-isocyanurate contained in the interior of the crystals will be as small as from 2 to 5 wt %. And, with such crystals, the remaining epichlorohydrin can be reduced to a level of at most 400 ppm simply by carrying out the drying in a gas stream under atmospheric pressure or under reduced pressure at a temperature of not higher than the melting point of the α-form tris-(2,3-epoxypropyl)-isocyanurate, such a from 40 to 120° C. by this method, the drying method can be simplified, although this method may be inferior from the viewpoint of the remaining epichlorohydrin as compared with the method of drying at a temperature of at least the melting point of the α-form tris-(2,3-epoxypropyl)-isocyanurate. However, with such crystals, the remaining epichlorohydrin can be reduced to a level of at most 300 ppm by drying at a temperature of at least the melting point of the α-form tris-(2,3-epoxypropyl)-isocyanurate (from 120 to 140° C.) in a gas stream under atmospheric pressure or under reduced pressure.

Method for Quantitative Analysis of the α-form Tris-(2,3-Epoxypropyl)-isocyanurate in the Interior of Crystals (1) The α-form tris-(2,3-epoxypropyl)-isocyanurate which can be extracted by methanol, is determined in such a manner that to the sample (crystals), 10 times of methanol is added, followed by stirring at 20° C. for 20 minutes, whereupon tris-(2,3-epoxypropyl)-isocyanurate in methanol is quantitatively analyzed by HPLC (high performance liquid chromatography).

Under this condition, if a value of at least 10 wt % is obtained, the treating temperature is changed from 20° C. to 40° C., and the measurement is carried out in the same manner, and the value will be taken as the measured value.

The tris-(2,3-epoxypropyl)-isocyanurate extractable by methanol is the α-form tris-(2,3-epoxypropyl)-isocyanurate present on the surface of the crystals.

(2) In the method for measuring the ratio of the α-form and the β-form in the entire crystals, a commercially available optical resolution column CHIRALPAK AD (manufactured by Daicel Chemical Industries, Ltd. (0.46 cm in diameter×25 cm in length)) was used for HPLC, n-hexane/2-propanol (40/60 v/v) is used as an eluting solution, the elution is carried out under such conditions that the column temperature is 24° C., and the flow rate is 1.0 ml/min, the sample crystals are dissolved in acetonitrile and further diluted with an eluting solution, and then poured into HPLC for chromatoseparation, whereby the β-form tris-(2,3-epoxypropyl)-isocyanurate will elute 11.00 minutes and 16.80 minutes, and the α-form tris-(2,3-epoxypropyl)-isocyanurate will elute 12.87 minutes and 14.20 minutes. The ratio of the α-form and the β-form in the entire crystals was calculated by the ratio of the areas of the respective peaks.

The α-form tris-(2,3-epoxypropyl)-isocyanurate which can not be extracted by methanol, can be calculated by the above (2)-(1). This α-form tris-(2,3-epoxypropyl)-isocyanurate which can not be extracted by methanol is believed to be the α-form tris-(2,3-epoxypropyl)-isocyanurate present in the interior of the β-form crystals.

Method for Quantitative Analysis of Unreacted Epichlorohydrin Remaining in the Crystals Unreacted epichlorohydrin remaining in the crystals is determined in such a manner that to the sample (the crystals), 20 times of dimethylformamide is added and dissolved by heating to 80° C., followed by quantitative analysis by gas chromatography.

Measurements of the Average Particle Size and the Particle Size Distribution

The measurements were carried out in a wet system using methanol as a dispersant by a laser diffraction light scattering particle size distribution measuring apparatus. As the average particle size, a volume standard median diameter D50 was used. As numerical values representing the distribution, the particle diameter at a 10% integrated volume (D10) and the particle diameter at a 90% integrated volume (D90) are shown.

Now, the present invention will be described in further detail with reference to Examples. However, it should be understood that the present invention is by no means restricted to such specific Examples.

EXAMPLE 1

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): A part of epichlorohydrin was distilled off under reduced pressure at a temperature of from 50 to 60° C. until the solid content concentration in the reaction solution became 40 wt %, to obtain 4,000 g of an adjusted liquid.

Step (C): The temperature was raised to 70° C. to completely dissolve the solid content, then the liquid was cooled to 60° C. over one hour, whereupon 11.2 g of β-form tris-(2,3-epoxypropyl)-isocyanurate having an average particle size of 45 μm was added as seed crystals (the number T of seed crystals was 1×10$^5$ particles/g).

Step (D): The liquid was stirred at 60° C. for one hour and then cooled to 25° C. over 4 hours to precipitate β-form tris-(2,3-epoxypropyl)-isocyanurate crystals, which were collected by filtration.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 700 ppm, an epoxy value of 101 g/eq., a content of α-form tris-(2,3-epoxypropyl)-isocyanurate extractable by methanol of 0.5 wt % and a content of α-form tris-(2,3-epoxypropyl)-isocyanurate not extractable by methanol contained in the interior of the crystals of 7.7 wt %. The crystals had a melting point of from 148 to 158° C., an average particle size of 75 μm, a particle size distribution being such that D10 was 12 μm, D50 was 75 μm and D90 was 180 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 180 ppm.

EXAMPLE 2

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 11.2 g of β-form tris-(2,3-epoxypropyl)-isocyanurate having an average particle size of 2.7 μm was added as seed crystals (the number T of the seed crystals was $4.9 \times 10^8$ particles/g).
Step (D): The operation was the same as in Example 1.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 290 g. The obtained crystals had an amount of remaining epichlorohydrin of 330 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 4.1 wt %, and the crystals had a melting point of from 149 to 158° C., an average particle size of 15 μm and a particle size distribution being such that D10 was 8 μm, D50 was 15 μm and D90 was 25 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 190 ppm.

EXAMPLE 3

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 24.0 g of β-form tris-(2,3-epoxypropyl)-isocyanurate having an average particle size of 2.7 μm was added as seed crystals (the number T of the seed crystals was $1.05 \times 10^9$ particles/g).
Step (D): The operation was the same as in Example 1.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 310 g. The obtained crystals had an amount of remaining epichlorohydrin of 270 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 3.2 wt %, and the crystals had a melting point of from 149 to 158° C., an average particle size of 12 μm and a particle size distribution being such that D10 was 7 μm, D50 was 12 μm and D90 was 20 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 230 ppm.

EXAMPLE 4

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 5.6 g of β-form tris-(2,3-epoxypropyl)-isocyanurate having an average particle size of 2.7 μm was added as seed crystals (the number T of the seed crystals was $2.45 \times 10^8$ particles/g).
Step (D): The operation was the same as in Example 1.
Step (E): The obtained crystals were washed with 1,200 g of methanol, followed by filtration. The obtained cake as dried at 80° C. under a reduced pressure of 5 Torr for hours to obtain β-form tris-(2,3-epoxypropyl)-isocyanurate crystals in a yield of 290 g. The obtained crystals had an amount of remaining epichlorohydrin of 400 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 5.0 wt %, and the crystals had a melting point of from 149 to 158° C., an average particle size of 18 μm and a particle size distribution being such that D10 was 9 μm, D50 was 18 μm and D90 was 35 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 190 ppm.

EXAMPLE 5

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 1.1 g of β-form tris-(2,3-epoxypropyl)-isocyanurate having an average particle size of 2.7 μm was added as seed crystals (the number T of the seed crystals was $4.9 \times 10^7$ particles/g).
Step (D): The operation was the same as in Example 1.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 520 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 7.4 wt %, and the crystals had a melting point of from 148 to 158° C., an average particle size of 27 μm and a particle size distribution being such that D10 was 11 μm, D50 was 27 μm and D90 was 55 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 130 ppm.

EXAMPLE 6

Step (A): The operation was the same as in Example 1.
Step (B): The operation was the same as in Example 1.

Step (C): The temperature was raised to 70° C. to completely dissolve the solid content, and then the liquid was cooled to 60° C. over one hour, and 0.16 g of β-form tris-(2,3-epoxypropyl)-isocyanurate having an average particle size of 2.7 μm was added as seed crystals (the number T of the seed crystals was 7×10$^6$ particles/g).

Step (D): The operation was the same as in Example 1.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 640 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 6.9 wt %, and the crystals had a melting point of from 148 to 158° C., an average particle size of 32 μm and a particle size distribution being such that D10 was 11 μm, D50 was 32 μm and D90 was 70 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 170 ppm.

EXAMPLE 7 step (A): The operation was the same as in Example 1.

Step (B): A part of epichlorohydrin was distilled off under reduced pressure at a temperature of from 50 to 60° C. until the solid content concentration in the reaction solution became 25 wt %, to obtain 6,400 g of an adjusted liquid.

Step (C): The temperature was raised to 53° C. to completely dissolve the solid content, and then the liquid was cooled to 43° C. over one hour, and 11.2 g of β-form tris-(2,3-epoxypropyl)-isocyanurate having an average particle size of 45 μm was added as seed crystals (the number T of the seed crystals was 1×10$^5$ particles/g).

Step (D): The liquid was stirred at 42° C. for one hour and then cooled to 10° C. over 4 hours to precipitate β-form tris-(2,3-epoxypropyl)-isocyanurate crystals, which were collected by filtration.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 800 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 6.8 wt %, and the crystals had a melting point of from 148 to 158° C., an average particle size of 75 μm and a particle size distribution being such that D10 was 17 μm, D50 was 75 μm and D90 was 160 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 170 ppm.

EXAMPLE 8

Step (A): The operation was the same as in Example 1.

Step (B): A part of epichlorohydrin was distilled off under reduced pressure at a temperature of from 50 to 60° C. until the solid content concentration in the reaction solution became 15 wt %, to obtain 10,700 g of an adjusted liquid.

Step (C): The temperature of the reaction system was raised to 40° C. to completely dissolve the solid content, and then the liquid was cooled to 30° C. over one hour, and 11.2 g of β-form tris-(2,3-epoxypropyl)-isocyanurate having an average particle size of 45 μm was added as seed crystals (the number T of the seed crystals was 1×10$^5$ particles/g).

Step (D): The liquid was stirred at 30° C. for one hour and then cooled to 0° C. over 4 hours to precipitate β-form tris-(2,3-epoxypropyl)-isocyanurate crystals, which were collected by filtration.

step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 260 g. The obtained crystals had an amount of remaining epichlorohydrin of 700 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 7.0 wt %, and the crystals had a melting point of from 148 to 158° C., an average particle size of 70 μm and a particle size distribution being such that D10 was 15 μm, D50 was 70 μm and D90 was 150 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 180 ppm.

EXAMPLE 9

Step (A): The operation was the same as in Example 1.

Step (B): The operation was the same as in Example 1.

Step (C): The temperature was raised to 70° C. to completely dissolve the solid content, and then the liquid was cooled to 60° C. over one hour, and 11.2 g of β-form tris-(2,3-epoxypropyl)-isocyanurate was added as seed crystals (the number T of the seed crystals was 1×10$^5$ particles/g).

Step (D): The liquid was immediately cooled to 25° C. over 5 hours without maintaining it at the temperature of the addition, to precipitate β-form tris-(2,3-epoxypropyl)-isocyanurate crystals, which were collected by filtration.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 270 g. The obtained crystals had an amount of remaining epichlorohydrin of 750 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 7.3 wt %, and the crystals had a melting point of from 148 to 158° C., an average particle size of 70 μm and a particle size distribution being such that D10 was 15 μm, D50 was 70 μm and D90 was 150 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 185 ppm.

EXAMPLE 10

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 11.2 g of β-form tris-(2,3-epoxypropyl)-isocyanurate crystals having an average particle size of 45 μm was added as seed crystals (the number T of the seed crystals was 1×10$^5$ particles/g).
Step (D): The liquid was maintained for 30 minutes at the above addition temperature of 60° C. and then cooled to 25° C. over two hours to precipitate β-form tris-(2,3-epoxypropyl)-isocyanurate crystals, which were collected by filtration.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 275 g. The obtained crystals had an amount of remaining epichlorohydrin of 800 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 7.7 wt %, and the crystals had a melting point of from 148 to 158° C., an average particle size of 65 μm and a particle size distribution being such that D10 was 15 μm, D50 was 65 μm and D90 was 140 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 165 ppm.

EXAMPLE 11

Step (A): The operation was the same as in Example 1.
Step (B): The operation was the same as in Example 1.
Step (C): The temperature before crystallization was 55° C., and at this temperature, the solid component in the adjusted liquid was not completely dissolved, but 1.1 g of β-form tris-(2,3-epoxypropyl)-isocyanurate crystals having an average particle size of 45 μm was added as seed crystals (the number T of the seed crystals was 1.0×10$^4$ particles/g)
Step (D): The liquid was stirred at a temperature of 55° C. for one hour and then cooled to 25° C. over 4 hours to precipitate β-form tris-(2,3-epoxypropyl)-isocyanurate crystals, which were collected by filtration.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 260 g. The obtained crystals had an amount of remaining epichlorohydrin of 700 ppm, an epoxy value of 103 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 5.0 wt %, and the crystals had a melting point of from 147 to 158° C., an average particle size of 50 μm and a particle size distribution being such that D10 was 12 μm, D50 was 50 μm and D90 was 230 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 220 ppm.

Example 11 was further repeated twice. The physical property values of the obtained crystals are shown below.

In the second time, β-form tris-(2,3-epoxypropyl)-isocyanurate crystals were obtained in a yield of 265 g. The crystals had an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 6.5 wt %, and the crystals had a melting point of from 148 to 158° C., an average particle size of 100 μm and a particle size distribution being such that D10 was 15 μm, D50 was 100 μm and D90 was 250 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 190 ppm.

In the third time, β-form tris-(2,3-epoxypropyl)-isocyanurate crystals were obtained in a yield of 260 g. The crystals had an epoxy value of 105 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 4.3 wt %, and the crystals had a melting point of from 146 to 157° C., an average particle size of 40 μm and a particle size distribution being such that D10 was 13 μm, D50 was 40 μm and D90 was 220 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 290 ppm.

EXAMPLE 12

Step (A): The operation was the same as in Example 1.
Step (B): The operation was the same as in Example 1.
Step (C): The temperature was raised to 70° C. to completely dissolve the solid content, and then the liquid was cooled to 60° C. over one hour, and 11.2 g of β-form tris-(2,3-epoxypropyl)-isocyanurate having an average particle size of 45 μm was added as seed crystals (the number T of the seed crystals was 1×10$^5$ particles/g).
Step (D): The liquid was stirred at a temperature of 60° C. for one hour and then cooled to 25° C. over 4 hours to precipitate β-form tris-(2,3-epoxypropyl)-isocyanurate crystals. During the crystallization, precipitation of crystals was carried out while applying supersonic waves to the solution by means of Model NS-200 Ultra Sonic Generator, manufactured by NISSEI K.K., and the crystals were collected by filtration.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 265 g. The obtained crystals had an amount of remaining epichlorohydrin of 400 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 4.0 wt %, and the crystals had a melting point of from 148 to 158° C., an average particle size of 17 μm and a particle size distribution being such that D10 was 12 μm, D50 was 17 μm and D90 was 30 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 230 ppm.

EXAMPLE 13

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 18 g of a tetraethylammonium bromide aqueous solution having a concentration of 60 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted under a reduced pressure of from 100 to 60 Torr for 6 hours while maintaining the temperature at 50° C. with stirring for dehydrochlorination Then, formed sodium chloride was, dissolved and washed by an addition of 3,600 g of water, followed by liquid separation, and further washed by an addition of 1,200 g of a 5 wt % sodium dihydrogen phosphate aqueous solution to neutralize sodium hydroxide used in an excess amount, followed by washing with 4,800 g of water.

Step (B): A part of epichlorohydrin was distilled off under reduced pressure at a temperature of from 50 to 60° C. until the solid content concentration in the reaction solution became 40 wt % to obtain 4,000 g of an adjusted liquid.

Step (C): The temperature was raised to 70° C. to completely dissolve the solid content, and then the liquid was cooled to 60° C. over one hour, and 36.0 g of high purity tris-(2,3-epoxypropyl)-isocyanurate (tradename TEPIC-S, manufactured by Nissan Chemical Industries, Ltd.) having an average particle size of 90 μm was added as seed crystals (the number T of the seed crystals was $9 \times 10^4$ particles/g).

Step (D): The liquid was stirred at 60° C. for one hour and then cooled to 25° C. over 4 hours to precipitate β-form tris-(2,3-epoxypropyl)-isocyanurate crystals, which were collected by filtration.

Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 280 g. The obtained crystals had an amount of remaining epichlorohydrin of 650 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 6.5 wt %, and the crystals had a melting point of from 148 to 158° C., an average particle size of 70 μm and a particle size distribution being such that D10 was 20 μm, D50 was 70 μm and D90 was 150 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 180 ppm.

EXAMPLE 14

Step (A): The operation was the same as in Example 1
Step (B): The operation was the same as in Example 1.
Step (C): The temperature was raised to 70° C. to completely dissolve the solid content, and then the liquid was cooled to 60° C. over one hour, and 1.1 g of β-form tris-(2,3-epoxypropyl)-isocyanurate having an average particle size of 100 μm was added as seed crystals (the number T of the seed crystals was $1 \times 10^3$ particles/g).
Step (D): The liquid was stirred at 60° C. for one hour and then cooled to 25° C. over 4 hours to precipitate β-form tris-(2,3-epoxypropyl)-isocyanurate crystals, which were collected by filtration.
Step (E): The obtained crystals were washed with 1,200 g of methanol, followed by filtration. The obtained cake was dried at 80° C. under a reduced pressure of 5 Torr for 4 hours to obtain β-form tris-(2,3-epoxypropyl)-isocyanurate crystals in a yield of 240 g. The obtained crystals had an amount of remaining epichlorohydrin of 850 ppm, an epoxy value of 101 g/eq., a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 8.0 wt %, and the crystals had a melting point of from 147 to 158° C., an average particle size of 110 μm and a particle size distribution being such that D10 was 40 μm, D50 was 110 μm and D90 was 200 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amount of remaining epichlorohydrin was 200 ppm.

Comparative Example 1

Step (A): Into a flask equipped with a stirrer and a thermometer, 129 g (1 mol) of cyanuric acid, 1,369 g (14.8 mols) of epichlorohydrin and 2.0 g of dimethylaniline were added and refluxed with stirring at 110° C. for 3.5 hours to carry out the reaction. Then, the temperature of the reaction system was cooled to 25° C., and 129 g (3.2 mols) of powdery sodium hydroxide was added while maintaining the temperature at from 25 to 30° C. with stirring for dehydrochlorination. Then, formed sodium chloride was removed by filtration, and 200 g of a 5 wt % sodium dihydrogen phosphate aqueous solution was added to the filtrate, followed by washing to neutralize sodium hydroxide used in an excess amount, followed by washing with 600 g of water.
Step (B): A part of epichlorohydrin was distilled off under reduced pressure at a temperature of from 50 to 55° C. until the solid content concentration in the reaction solution became 55 wt %, to obtain 480 g of an adjusted liquid.
Step (D): Crystallization was initiated at 55° C., and the liquid was cooled to 20° C. over 4 hours and left to stand still at that temperature for 4 hours, whereupon precipitated white crystals were collected by filtration.
Step (E): The obtained crystals methanol, followed by 340 g of methanol, followed by filtration. The obtained cake was dried at 80° C. under a reduced pressure of 5 Torr for 4 hours to obtain tris-(2,3-epoxypropyl)-isocyanurate crystals in a yield of 84 g. The obtained crystals had an amount of remaining epichlorohydrin of 2,900 ppm, an epoxy value of 105 g/eq., a content of α-form tris-(2,3-epoxypropyl)-isocyanurate extractable by methanol of 21 wt %, and a content of α-form tris-(2,3-epoxypropyl)-isocyanurate not extractable by methanol contained in the interior of the crystals of 19 wt %, and the crystals had a melting point of from 120 to 148° C., an average particle size of 20 μm and a particle size distribution being such that D10 was 2 μm, D50 was 20 μm and D90 was 100 μm, and they were white crystals. Further, the crystals were dried in a nitrogen stream at 130° C. under a reduced pressure of 10 Torr by a rotary evaporator for 24 hours, whereby the amount of remaining epichlorohydrin in the obtained crystals was 1,800 ppm. Further, the crystals were coagulated, as particles were partially connected to one another by α-form tris-(2,3-epoxypropyl)-isocyanurate melted during the drying at 130° C.

Comparative Example 2

Step (A): Into a flask equipped with a stirrer and a thermometer, 129 g (1 mol) of cyanuric acid, 1,190 g (12.9 mols) of epichlorohydrin and 1.0 g of triethylamine were added and refluxed with stirring at from 110 to 115° C. for 3.0 hours to carry out the reaction. Then, the temperature of the reaction system was cooled to from 30 to 35° C., and 190 g (3.4 mols) of powdery potassium hydroxide was added every 30 minutes in five times in an equal amount while maintaining the temperature at from 25 to 30° C. for dehydrochlorination. Then, formed potassium chloride was removed by filtration, and 200 g of a 5 wt % sodium dihydrogen phosphate aqueous solution was added to the filtrate, followed by washing to neutralize sodium hydroxide used in an excess amount, followed by washing with 600 g of water.

Step (B): A part of epichlorohydrin was distilled off under reduced pressure at a temperature of from 60 to 65° C. until the solid content concentration in the reaction solution became 60 wt %, to obtain 440 g of an adjusted liquid.

Step (D): Crystallization was initiated at 65° C., and the liquid was cooled to 25° C. over 4 hours and stirred at that temperature 5 hours, whereupon precipitated white crystals were collected by filtration.

Step (E): The obtained crystals were washed with 320 g of methanol, followed by filtration. The obtained cake was dried at 80° C under a reduced pressure of 5 Torr for 4 hours to obtain tris-(2,3-epoxypropyl)-isocyanurate crystals in a yield of 80 g. The obtained crystals had an amount of remaining epichlorohydrin of 2,700 ppm, an epoxy value of 104 g/eq., a content of α-form tris-(2,3-epoxypropyl)-isocyanurate extractable by methanol of 22 wt %, and a content of α-form tris-(2,3-epoxypropyl)-isocyanurate not extractable by methanol contained in the interior of the crystals of 20 wt %, and the crystals had a melting point of from 118 to 148° C., an average particle size of 18 μm and a particle size distribution being such that D10 was 2 μm, D50 was 18 μm and D90 was 90 μm, and they were white crystals. Further, the crystals were dried in a nitrogen stream at 130° C. under a reduced pressure of 10 Torr by a rotary evaporator for 24 hours, whereby the amount of remaining epichlorohydrin in the obtained crystals was 1,700 ppm. Further, the crystals were coagulated as the particles were partially connected to one another by α-form tris-(2,3-epoxypropyl)-isocyanurate melted during the drying at 130° C.

Comparative Example 3

Step (A): Into a flask equipped with a stirrer and a thermometer, 129 g (1 mol) of cyanuric acid, 1,250 g (13.5 mols) of epichlorohydrin and 3.0 g of a 60 wt % tetraethylammonium bromide aqueous solution, were added and refluxed with stirring at 110° C. for 3.5 hours to carry out the reaction. Then, the temperature of the reaction system was cooled to from 20 to 30° C., and 129 g (3.2 mols) of powdery sodium hydroxide was added with stirring for dehydrochlorination. Then, formed sodium chloride was removed by filtration, and 200 g of a 5 wt % sodium dihydrogen phosphate aqueous solution was added to the filtrate, followed by washing to neutralize sodium hydroxide used in an excess amount, followed by washing with 600 g of water.

Step (B): A part of epichlorohydrin was distilled off under reduced pressure at a temperature of from 50 to 60° C. until the solid content concentration in the reaction solution became 50 wt %, to obtain 540 g of an adjusted liquid.

Step (D): Crystallization was initiated at 55° C., and the liquid was cooled to 25° C. over 4 hours and stirred at that temperature for 4.5 hours, whereupon precipitated white crystals were collected by filtration.

Step (E): The obtained crystals were washed with 350 g of methanol, followed by filtration. The obtained cake was dried at 80° C. under a reduced pressure of 5 Torr for 4 hours to obtain tris-(2,3-epoxypropyl)-isocyanurate crystals in a yield of 88 g. The obtained crystals had an amount of remaining epichlorohydrin of 2,200 ppm, an epoxy value of 103 g/eq., a content of α-form tris-(2,3-epoxypropyl)-isocyanurate extractable by methanol of 21 wt %, and a content of α-form tris-(2,3-epoxypropyl)-isocyanurate not extractable by methanol contained in the interior of the crystals of 19 wt %, and the crystals had a melting point of from 118 to 148° C., an average particle size of 15 μm and a particle size distribution being such that D10 was 2 μm, D50 was 15 μm and D90 was 85 μm, and they were white crystals. Further, the crystals were dried in a nitrogen stream at 130° C. under a reduced pressure of 10 Torr by a rotary evaporator for 24 hours, whereby the amount of remaining epichlorohydrin in the obtained crystals was 1,600 ppm. Further, the crystals were coagulated as the particles were partially connected to one another by α-form tris-(2,3-epoxypropyl)-isocyanurate melted during the drying at 130° C.

Comparative Example 4

Step (A): Into a flask equipped with a stirrer and a thermometer, 129 g (1 mol) of cyanuric acid, 1,388 g (15.0 mols) of epichlorohydrin and 3.0 g of a 60 wt % tetraethylammonium bromide aqueous solution, were added and refluxed with stirring at 110° C. for 3.5 hours to carry out the reaction. Then, the temperature of the reaction system was cooled to from 40 to 50° C., and 256 g (3.2 mols) of a 50 wt % sodium hydroxide aqueous solution was added while maintaining the temperature at from 40 to 50° C. with stirring to carry out dehydrochlorination under a reduced pressure of from 110 to 60 Torr for 6 hours. Then, formed sodium chloride was dissolved by an addition of 300 g of water and thereby washed, followed by liquid separation, and 100 g of a 5 wt % sodium dihydrogen phosphate aqueous solution was further added for washing to neutralize sodium hydroxide used in an excess amount, followed by washing with 300 g of water.

Step (B): A part of epichlorohydrin was distilled off under reduced pressure at a temperature of from 65 to 70° C.

until the solid content concentration in the reaction solution became 60 wt %, to obtain 440 g of an adjusted liquid.

Step (D): Crystallization was initiated at 70° C., and the liquid was cooled to 20° C. over 5 hours and left to stand still at that temperature for 4 hours, whereupon precipitated white crystals were collected by filtration.

Step (E): The obtained crystals were washed with 320 g of methanol, followed by filtration. The obtained cake was dried at 80° C. under a reduced pressure of 5 Torr for 4 hours to obtain tris-(2,3-epoxypropyl)-isocyanurate crystals in a yield of 80 g. The obtained crystals had an amount of remaining epichlorohydrin of 2,000 ppm, an epoxy value of 102 g/eq., a content of α-form tris-(2,3-epoxypropyl)-isocyanurate extractable by methanol of 21 wt %, and a content of α-form tris-(2,3-epoxypropyl)-isocyanurate not extractable by methanol contained in the interior of the crystals of 18 wt %, and the crystals had a melting point of from 120 to 148° C., an average particle size of 18 μm and a particle size distribution being such that D10 was 2 μm, D50 was 18 μm and D90 was 90 μm, and they were white crystals. Further, the crystals were dried in a nitrogen stream at 130° C. under a reduced pressure of 10 Torr by a rotary evaporator for 24 hours, whereby the amount of remaining epichlorohydrin in the obtained crystals was 1,600 ppm. Further, the crystals were coagulated as the particles were partially connected to one another by α-form tris-(2,3-epoxypropyl)-isocyanurate melted during the drying at 130° C.

Comparative Example 5

Step (A): The operation was the same as in Comparative Example 4.

Step (B): A part of epichlorohydrin was distilled off under reduced pressure at a temperature of from 60 to 70° C. until the solid content concentration in the reaction solution became 50 wt %, to obtain 530 g of an adjusted liquid.

Step (D): Crystallization was initiated at 60° C., and the liquid was cooled to 25° C. over 4 hours and stirred at that temperature for 4 hours, whereupon precipitated white crystals were collected by filtration.

Step (E): The obtained crystals were washed with 280 g of methanol, followed by filtration. The obtained cake was dried at 80° C. under a reduced pressure of 5 Torr for 4 hours to obtain tris-(2,3-epoxypropyl)-isocyanurate crystals in a yield of 76 g. The obtained crystals had an amount of remaining epichlorohydrin of 2,500 ppm, an epoxy value of 102 g/eq., a content of α-form tris-(2,3-epoxypropyl)-isocyanurate extractable by methanol of 14 wt %, and a content of α-form tris-(2,3-epoxypropyl)-isocyanurate not extractable by methanol contained in the interior of the crystals of 18 wt %, and the crystals had a melting point of from 138 to 150° C., an average particle size of 16 μm and a particle size distribution being such that D10 was 2 μm. D50 was 16 μm and D90 was 95 μm, and they were white crystals. Further, the crystals were dried in a nitrogen stream at 130° C. under a reduced pressure of 10 Torr by a rotary evaporator for 24 hours, whereby the amount of remaining epichlorohydrin in the obtained crystals was 1,500 ppm. Further, the crystals were coagulated as the particles were partially connected to one another by α-form tris-(2,3-epoxypropyl)-isocyanurate melted during the drying at 130° C.

Comparative Example 6

Step (A): The operation was the same as in Comparative Example 5.

Step (B): The operation was the same as in Comparative Example 5.

Step (D): The operation was the same as in Comparative Example 5.

Step (E): The obtained crystals were collected by filtration and then washed with 280 g of methanol, and 500 g of epichlorohydrin was added, followed by heating to 70° C. to dissolve the crystals. Then, the liquid was cooled to 25° C. over 5 hours to recrystallize the crystals. The crystals were washed with 250 g of methanol and then dried at 80° C. under a reduced pressure of 5 Torr for 4 hours to obtain β-form tris-(2,3-epoxypropyl)-isocyanurate crystals in a yield of 52.6 g. The crystals had an average particle size of 300 μm, the remaining epichlorohydrin was 2,500 ppm, and the α-form tris-(2,3-epoxypropyl)-isocyanurate which was considered to be attached to the surface of crystals, extractable by methanol, was 0.5 wt %, and the α-form tris-(2,3-epoxypropyl)-isocyanurate contained in the interior of the crystals was 1 wt %. The crystals had a melting point of from 150 to 158° C., an average particle size of 300 μm and a particle size distribution being such that D10 was 100 μm, D50 was 300 μm and D90 was 500 μm. Further, the crystals were dried at 130° C. under a reduced pressure of 10 Torr for 24 hours, whereby the remaining epichlorohydrin in the obtained crystals was 2,500 ppm. This is believed that since a predetermined amount of α-form tris-(2,3-epoxypropyl)-isocyanurate was not present in the interior of the crystals, liquid pores were not formed in the crystals during the drying step at 130° C., and epichlorohydrin remained without being removed from the crystals.

Comparative Example 7

Step (A): The operation was the same as in Comparative Example 1.

Step (B): The operation was the same as in Comparative Example 1.

Step (D): The operation was the same as in Comparative Example 1.

Step (E): The obtained crystals were washed with 1,700 g of methanol, followed by filtration. The obtained cake was dried at 80° C. under a reduced pressure of 5 Torr for 4 hours to obtain tris-(2,3-epoxypropyl)-isocyanurate crystals in a yield of 71 g. The obtained crystals had an amount of remaining epichlorohydrin of 2,500 ppm, an epoxy value of 104 g/eq., a content of α-form tris-(2,3-epoxypropyl)-isocyanurate extractable by methanol of 6 wt %, and a content of α-form tris-(2,3-epoxypropyl)-isocyanurate not extractable by methanol contained in the interior of the crystals of 23 wt %, and the crystals had a melting point of from 128 to 149° C., an average particle size of 20 μm and a particle size distribution being such that D10 was 2 μm, D50 was 20 μm and D90 was 100 μm, and they were white crystals. Further, the crystals were dried at 130° C. under a reduced pressure of 10 Torr for 24 hours, whereby the amount of remaining epichlorohydrin in the obtained crystals was 1,700 ppm. Further, the crystals were coagulated as the particles were partially connected to one another by α-form tris-(2,3-epoxypropyl)-isocyanurate melted during the drying at 130° C.

Comparative Example 8

Step (A): The operation was the same as in Comparative Example 4.

Step (B): The operation was the same as in Comparative Example 4.

Step (D): The operation was the same as in Comparative Example 4.

Step (E): The obtained crystals were washed with 1,600 g of methanol, followed by filtration. The obtained cake was dried at 80° C. under a reduced pressure of 5 Torr for 4 hours to obtain tris-(2,3-epoxypropyl)-isocyanurate crystals in a yield of 66 g. The obtained crystals had an amount of remaining epichlorohydrin of 1,800 ppm, an epoxy value of 102 g/eq., a content of α-form tris-(2,3-epoxypropyl)-isocyanurate extractable by methanol of 6 wt %, and a content of α-form tris-(2,3-epoxypropyl)-isocyanurate not extractable by methanol contained in the interior of the crystals of 21.4 wt %, and the crystals had a melting point of from 141 to 151° C., an average particle size of 18 μm and a particle size distribution being such that D10 was 2 μm, D50 was 18 μm and D90 was 90 μm. and they were white crystals. Further, the crystals were dried at 130° C. under a reduced pressure of 10 Torr for 24 hours, whereby the amount of remaining epichlorohydrin in the obtained crystals was 1,500 ppm. Further, the crystals were coagulated as the particles were partially connected to one another by α-form tris-(2,3-epoxypropyl)-isocyanurate melted during the drying at 130° C.

In Examples 2 to 4, the number of seed crystals added was large, and in Example 12, ultrasonic waves were applied during the crystallization. Accordingly, in these Examples, the average particle size of the obtained crystals was small, the amounts of remaining epichlorohydrin and α-form tris-(2,3-epoxypropyl)-isocyanurate were small even by drying at a temperature of about 80° C. only. This is believed attributable to the fact that by the large specific surface area, epichlorohydrin and α-form tris-(2,3-epoxypropyl)-isocyanurate are removed during the crystallization process and the washing process. Further, it is believed that with such fine particles, formation of particles proceeds slowly, whereby the amounts of epichlorohydrin and α-form tris-(2,3-epoxypropyl)-isocyanurate taken into the interior of the crystals will be small.

In Examples 1, 5 to 11 and 13 to 15, the amount of remaining epichlorohydrin present in the finally obtainable particles is not more than 300 ppm, since it is considered that even with particles having remaining epichlorohydrin of about 400 to 900 ppm during the drying at 80° C., α-form tris-(2,3-epoxypropyl)-isocyanurate present in the interior of the crystals will form liquid pores of α-form tris-(2,3-epoxypropyl)-isocyanurate melted in the pores by the drying temperature of about 130° C., and epichlorohydrin is removed through such pores. Further, the molten α-form tris-(2,3-epoxypropyl)-isocyanurate content is from 2 to 15 wt %, whereby it will scarcely bleed out of the crystals, and coagulation scarcely takes place.

In Comparative Examples 1 to 5 wherein the process of the present invention employing seed crystals is not used, rapid crystallization occurs by a slight temperature change even if gradual cooling is carried out during the cooling step, whereby large amount of epichlorohydrin and α-form tris-(2,3-epoxypropyl)-isocyanurate are taken into the interior of the crystals, whereby the purity of the crystals deteriorates. If the α-form is present in the interior of the crystals in an amount exceeding 15 wt %, the amount of the α-form melting during the drying step of about 130° C. will be large, the crystals themselves will not be able to maintain a particulate state, whereby coagulation of particles by the molten α-form is likely to take place.

Further, a large amount of the α-form is present outside the crystals, and can not efficiently be removed even by washing with methanol in an amount of 4 times by weight or more relative to the tris-(2,3-epoxypropyl)-isocyanurate. Such a large amount of the α-form will also melt during the drying step at a temperature of about 130° C. and serves as a binder, whereby the particles tend to fuse to one another, leading to coagulation.

If such coagulation takes place, the product will be large blocks on the drying line in step (E) and may stop the production line in the process for producing β-form tris-(2, 3-epoxypropyl)-isocyanurate crystals, such being undesirable.

The β-form tris-(2,3-epoxypropyl)-isocyanurate crystals containing α-form tris-(2,3-epoxypropyl)-isocyanurate in the interior of the crystals of the present invention, are obtainable by an operation wherein seed crystals are added to the reaction solution obtained in step (A), whereby they can easily be prepared even in the production on an industrial scale.

Such crystals have a low content of epichlorohydrin due to the α-form tris-(2,3-epoxypropyl)-isocyanurate contained in the interior. Namely, the α-form tris-(2,3-epoxypropyl)-isocyanurate present in the interior of the crystals will melt to form liquid pores during the drying at a temperature of about 130° C., and epichlorohydrin is discharged out of the crystals through such pores, but the liquid α-form tris-(2,3-epoxypropyl)-isocyanurate in the liquid state in the interior of the crystals will not bleed out of the crystals during heating at a temperature of about 130° C., whereby coagulation of particles to one another scarcely takes place. Further, the α-form tris-(2,3-epoxypropyl)-isocyanurate in the interior of the crystals will not be eluted out of the crystals even by a solvent.

The β-form tris-(2,3-epoxypropyl)-isocyanurate crystals obtained by the present invention contains small amounts of α-form tris-(2,3-epoxypropyl)-isocyanurate extractable by an alcohol and epichlorohydrin hazardous to human bodies and to applications to electronic materials and highly purified, and they can be used in the field of e.g. a photosetting/thermosetting combined resist ink utilizing such characteristics.

What is claimed is:

1. β-form tris-(2,3-epoxypropyl)-isocyanurate crystals, each of the crystals having a surface and an interior, said crystals containing from 2 to 15 wt % of α-form tris-(2,3-epoxypropyl)-isocyanurate in the interior.

2. The β-form tris-(2,3-epoxypropyl)-isocyanurate crystals according to claim 1, which have an average particle size of from 10 to 500 μm.

3. A process for producing β-form tris-(2,3-epoxypropyl)-isocyanurate crystals containing from 2 to 15 wt % of α-form tris-(2,3-epoxypropyl)-isocyanurate in the interior of the crystals, which comprises the following steps (A), (B), (C), (D) and (E):

(A) a step of reacting 1 mol of cyanuric acid with from 5 to 180 mols of epichlorohydrin to form an addition product of cyanuric acid and epichlorohydrin, followed by dehydrochlorination to obtain a reaction solution containing tris-(2,3-epoxypropyl)-isocyanurate, (B) a step of adjusting the reaction solution containing tris-(2,3-epoxypropyl)-isocyanurate obtained in step (A) to a solid content concentration of from 10 to 50 wt %, (C) a step of adding seed crystals to the liquid obtained in step (B) at a temperature lower by from 5 to 20° C. than the temperature at which the liquid forms a saturated solution, (D) a step of gradually cooling the liquid obtained in step (C) at a cooling rate of not higher than 20° C./hr for crystallization, followed by filtration to obtain crystals, and (E) a step of washing and drying the crystals obtained in step (D).

4. The process according to claim 3, wherein step (A) is a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a trisubstituted phosphine and a quaternary phosphonium salt, as catalyst, to obtain a reaction solution, adding from 2 to 6 mols of an alkali metal hydroxide or an alkali metal alcoholate to the reaction solution for dehydrochlorination, and then removing the resulting alkali metal salt to obtain a reaction solution containing tris-(2,3-epoxypropyl)-isocyanurate.

5. The process according to claim 3, wherein step (C) is a step of heating the liquid obtained in step (B) to a temperature of at least the temperature at which the liquid forms a saturated solution, thereafter cooling the liquid to a temperature lower by from 5 to 20° C. than the temperature at which the liquid forms a saturated solution, and then adding seed crystals thereto.

6. The process according to claim 3, wherein the addition of seed crystals in step (C) satisfies the following formulae (1) and (2):

$$1\times10^{10} \geq T \geq 1\times10^2 \qquad (1)$$

$$T = 1.4\times10^{12}(m/(M\times D^3)) \qquad (2)$$

wherein T is the number of seed crystals added per the weight of tris-(2,3-epoxypropyl)-isocyanurate in the reaction solution (number/g), m is the amount of seed crystals added (g), D is the average particle size of seed crystals which is from 2 to 300 μm, and M is the weight (g) of tris-(2,3-epoxypropyl)-isocyanurate in the reaction solution.

7. The process according to claim 3, wherein the seed crystals added in step (C) is β-form tris-(2,3-epoxypropyl)-isocyanurate, or a mixture of β-form tris-(2,3-epoxypropyl)-isocyanurate and α-form tris-(2,3-epoxypropyl)-isocyanurate.

8. The process according to claim 3, further comprising the application, in step (D), of ultrasonic waves to the liquid obtained in step (C) during cooling.

9. The process according to claim 3, wherein in step (E) a solvent capable of providing a solubility of at least 0.5 g/100 g at 20° C. to α-form tris-(2,3-epoxypropyl)-isocyanurate and a solubility of less than 0.5 g/100 g at 20° C. to β-form tris-(2,3-epoxypropyl)-isocyanurate, is used in an amount of from 0.5 to 10 times by weight relative to the β-form tris-(2,3-epoxypropyl)-isocyanurate crystals.

10. The process according to claim 3, wherein the average particle size of the crystals obtained in step (D) is from 20 to 500 μm, and the drying in step (E) is carried out under atmospheric pressure or under reduced pressure at a temperature of from 120 to 140° C.

11. The process according to claim 3, wherein the average particle size of the crystals obtained in step (D) is from 10 to 20 μm and the drying in step (E) is carried out under atmospheric pressure or under reduced pressure at a temperature of from 40 to 120° C.

* * * * *

UNITED STATES PATENT AND TRADEMARK OFFICE
CERTIFICATE OF CORRECTION

PATENT NO. : 6,124,454

DATED : September 26, 2000

INVENTOR(S): Hisao IKEDA, et al.

It is certified that an error appears in the above-identified patent and that said Letters Patent is hereby corrected as shown below:

On the Title Page, Item [30], the Foreign Application Priority Data information is incorrect. Item [30] should read as follows:

--[30]  Foreign Application Priority Data

Apr. 20, 1998   [JP]   Japan ............................. 10-109204   --

Signed and Sealed this

Eighth Day of May, 2001

Attest:

NICHOLAS P. GODICI

Attesting Officer     *Acting Director of the United States Patent and Trademark Office*